United States Patent [19]

Fauchere et al.

[11] Patent Number: 5,786,330
[45] Date of Patent: Jul. 28, 1998

[54] PEPTIDE COMPOUNDS WHICH ARE THERAPEUTICALLY ACTIVE IN THE CASCADE OF BLOOD COAGULATION, PROCESS FOR PREPARING THEM AND PHARMACEUTICAL COMPOSITIONS CONTAINING THEM

[75] Inventors: Jean-Luc Fauchere, Saint-Cloud; Christophe Thurieau, Paris; Tony Verbeuren, Vernouillet; Alain Rupin, Savonnieres; Serge Simonet, Conflans Ste Honorine, all of France

[73] Assignee: Adir et Compagnie, Courbevoie, France

[21] Appl. No.: 619,683

[22] PCT Filed: Oct. 6, 1994

[86] PCT No.: PCT/FR94/01166

§ 371 Date: Apr. 2, 1996

§ 102(e) Date: Apr. 2, 1996

[87] PCT Pub. No.: WO95/09869

PCT Pub. Date: Apr. 13, 1995

[30] Foreign Application Priority Data

Oct. 7, 1993 [FR] France .................. 93 11942

[51] Int. Cl.$^6$ .................................. A61K 38/00
[52] U.S. Cl. .................. 514/13; 514/822; 530/326
[58] Field of Search .................. 530/326; 514/13, 514/822

[56] References Cited

U.S. PATENT DOCUMENTS 5,371,071  12/1994  Fauchere et al. .................. 514/14

FOREIGN PATENT DOCUMENTS

0552999A1  7/1993  European Pat. Off. .

OTHER PUBLICATIONS

Maraganore, et al., "Design and Characterization of Hirulogs: A Novel Class of Bivalent Peptide Inhibitors of Thrombin Biochemistry", vol. 29, No. 30, 7095–7101 Jul. 31, (1990).

Bourdon, et al., "Structure–function relationships of hirulog peptide interactions with thrombin", FEBS Letters, vol. 294, No. 3, 163–166, (Dec. 1991).

Krstenansky, et al., "Development of MDL 28,050, a Small Stable Antithrombin Agent Based on a Functional Domain of the Leech Protein, Hirudin", Thrombosis & Haemostasis, vol. 63, No. 2, 208–214, (1990).

Thurieau, et al., "Synthesis of a New Bivalent Hirudin Analog (Hirufos), which Includes a Stable 4'–Phosphono–L–phenylalanine Mimic of (L–Tyrosine O$^4$–Sulfate)–63", Helvetica Chimica ACTA, vol. 77, No. 3, 679–684 (May 11, 1994).

*Primary Examiner*—Cecilia J. Tsang
*Assistant Examiner*—C. Delacroix-Muirheid
*Attorney, Agent, or Firm*—The Firm of Gordon W. Hueschen

[57] ABSTRACT

The invention relates to the compounds of formula (I) (SEQ ID NO: I:

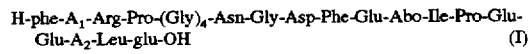

H-phe-A$_1$-Arg-Pro-(Gly)$_4$-Asn-Gly-Asp-Phe-Glu-Abo-Ile-Pro-Glu-Glu-A$_2$-Leu-glu-OH      (I)

in which A$_1$ and A$_2$ are as defined in the description. Medicinal products containing the same are useful as anticoagulants.

6 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 2
      ( D ) OTHER INFORMATION: /label=A1

( i x ) FEATURE:
    ( A ) NAME/KEY: Modified-site
    ( B ) LOCATION: 14
    ( D ) OTHER INFORMATION: /label=Abo
        / note="Abo=2-azabicyclo[2.2.2]octane-3-carbonyl"

( i x ) FEATURE:
    ( A ) NAME/KEY: Modified-site
    ( B ) LOCATION: 19
    ( D ) OTHER INFORMATION: /label=A2

( i x ) FEATURE:
    ( A ) NAME/KEY: Modified-site
    ( B ) LOCATION: 1
    ( D ) OTHER INFORMATION: /label=phe
        / note="D configuration"

( i x ) FEATURE:
    ( A ) NAME/KEY: Modified-site
    ( B ) LOCATION: 21
    ( D ) OTHER INFORMATION: /label=glu
        / note="D configuration"

( x i ) SEQUENCE DESCRIPTION: SEQ ID NO:1:

Phe Xaa Arg Pro Gly Gly Gly Gly Asn Gly Asp Phe Glu Xaa Ile Pro
1               5                   10                  15

Glu Glu Xaa Leu Glu
        20

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=phe
            / note="D configuration"

( i x ) FEATURE:
        ( A ) NAME/KEY: Modified-site
        ( B ) LOCATION: 14
        ( D ) OTHER INFORMATION: /label=Abo
            / note="SEE SEQ ID NO. 1"

( i x ) FEATURE:
        ( A ) NAME/KEY: Modified-site
        ( B ) LOCATION: 19
        ( D ) OTHER INFORMATION: /label=Phe
            / note="Phe(pPO3H2)"

( i x ) FEATURE:
        ( A ) NAME/KEY: Modified-site
        ( B ) LOCATION: 21
        ( D ) OTHER INFORMATION: /label=glu
            / note="D configuration"

( x i ) SEQUENCE DESCRIPTION: SEQ ID NO:2:

Phe Pro Arg Pro Gly Gly Gly Gly Asn Gly Asp Phe Glu Xaa Ile Pro
1               5                   10                  15

Glu Glu Xaa Leu Glu
        20

( 2 ) INFORMATION FOR SEQ ID NO:3:

( i ) SEQUENCE CHARACTERISTICS:
        ( A ) LENGTH: 21 amino acids
        ( B ) TYPE: amino acid ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=phe
        / note="D configuration"

( i x ) FEATURE:
    ( A ) NAME/KEY: Modified-site
    ( B ) LOCATION: 2
    ( D ) OTHER INFORMATION: /label=Oic
        / note="Oic=octahydroindole-2-carbonyl"

( i x ) FEATURE:
    ( A ) NAME/KEY: Modified-site
    ( B ) LOCATION: 14
    ( D ) OTHER INFORMATION: /label=Abo
        / note="SEE SEQ ID NO. 1"

( i x ) FEATURE:
    ( A ) NAME/KEY: Modified-site
    ( B ) LOCATION: 19
    ( D ) OTHER INFORMATION: /label=Phe
        / note="Phe(pPO3H2)"

( i x ) FEATURE:
    ( A ) NAME/KEY: Modified-site
    ( B ) LOCATION: 21
    ( D ) OTHER INFORMATION: /label=glu
        / note="D configuration"

( x i ) SEQUENCE DESCRIPTION: SEQ ID NO:3:

```
Phe Xaa Arg Pro Gly Gly Gly Gly Asn Gly Asp Phe Glu Xaa Ile Pro
 1               5                   10                  15

Glu Glu Phe Leu Glu
            20
```

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=phe
            / note="D configuration"

( i x ) FEATURE:
        ( A ) NAME/KEY: Modified-site
        ( B ) LOCATION: 2
        ( D ) OTHER INFORMATION: /label=Abh
            / note="Abh=2-azabicyclo[2.2.1]heptane-3-carbonyl"

( i x ) FEATURE:
        ( A ) NAME/KEY: Modified-site
        ( B ) LOCATION: 14
        ( D ) OTHER INFORMATION: /label=Abo
            / note="SEE SEQ ID NO. 1"

( i x ) FEATURE:
        ( A ) NAME/KEY: Modified-site
        ( B ) LOCATION: 19
        ( D ) OTHER INFORMATION: /label=Phe
            / note="Phe(pPOcH2)"

( i x ) FEATURE:
        ( A ) NAME/KEY: Modified-site
        ( B ) LOCATION: 21
        ( D ) OTHER INFORMATION: /label=glu / note="D configuration"

( x i ) SEQUENCE DESCRIPTION: SEQ ID NO:4:

Phe Xaa Arg Pro Gly Gly Gly Gly Asn Gly Asp Phe Glu Xaa Ile Pro
1               5                       10                      15

Glu Glu Phe Leu Glu
            20

( 2 ) INFORMATION FOR SEQ ID NO:5:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=phe
            / note="D configuration"

( i x ) FEATURE:
        ( A ) NAME/KEY: Modified-site
        ( B ) LOCATION: 2
        ( D ) OTHER INFORMATION: /label=Abo
            / note="SEE SEQ ID NO. 1"

( i x ) FEATURE:
        ( A ) NAME/KEY: Modified-site
        ( B ) LOCATION: 14
        ( D ) OTHER INFORMATION: /label=Abo
            / note="SEE SEQ ID NO. 1"

( i x ) FEATURE:
        ( A ) NAME/KEY: Modified-site
        ( B ) LOCATION: 19
        ( D ) OTHER INFORMATION: /label=Phe
            / note="Phe(pPO3H2)"

( i x ) FEATURE:
        ( A ) NAME/KEY: Modified-site
        ( B ) LOCATION: 21
        ( D ) OTHER INFORMATION: /label=glu
            / note="D configuration"

( x i ) SEQUENCE DESCRIPTION: SEQ ID NO:5:

Phe Xaa Arg Pro Gly Gly Gly Gly Asn Gly Asp Phe Glu Xaa Ile Pro
1               5                       10                      15

Glu Glu Phe Leu Glu
            20

( 2 ) INFORMATION FOR SEQ ID NO:6:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=phe
            / note="D configuration"

( i x ) FEATURE:
        ( A ) NAME/KEY: Modified-site
        ( B ) LOCATION: 14
        ( D ) OTHER INFORMATION: /label=Abo
            / note="SEE SEQ ID NO. 1"

```
( i x ) FEATURE:
        ( A ) NAME/KEY: Modified-site
        ( B ) LOCATION: 19
        ( D ) OTHER INFORMATION: /label=Phe
                / note="Phe(mPO3H2)"

( i x ) FEATURE:
        ( A ) NAME/KEY: Modified-site
        ( B ) LOCATION: 21
        ( D ) OTHER INFORMATION: /label=glu
                / note="D configuration"

( x i ) SEQUENCE DESCRIPTION: SEQ ID NO:6:

Phe  Pro  Arg  Pro  Gly  Gly  Gly  Gly  Asn  Gly  Asp  Phe  Glu  Xaa  Ile  Pro
1                   5                        10                       15

Glu  Glu  Phe  Leu  Glu
               20
```

PEPTIDE COMPOUNDS WHICH ARE THERAPEUTICALLY ACTIVE IN THE CASCADE OF BLOOD COAGULATION, PROCESS FOR PREPARING THEM AND PHARMACEUTICAL COMPOSITIONS CONTAINING THEM

TECHNICAL FIELD

The present invention relates to new peptide compounds which are therapeutically active in the cascade of blood coagulation.

PRIOR ART

It is now widely known that when the balance between procoagulant and anticoagulant factors in the blood is disrupted, it may lead to the formation of a thrombus or blood clot. The development of a thrombosis is essentially favored by three principal pathogenic factors which are stasis or decrease in blood flow, hypercoagulatability states and lesions of the endothelium of the vascular wall. Against these pathogeneses, it is therefore advisable to establish a treatment of which one of the principal bases is the anticoagulant drug.

Anticoagulants can indeed be used in the treatment of acute venous thromboses, pulmonary embolism, arterial embolism of the extremities, arterial thromboses such as myocardial infarction, atherosclerosis, all the other thromboembolic manifestations as well as for maintaining blood homeostasis, in particular in extracorporeal circulation.

Among the known anticoagulant agents, hirudin, which is a polypeptide comprising 65 amino acids, is a specific thrombin inhibitor isolated from the salivary glands of medicinal leeches (Biochemistry 25, 4622–28, 1986).

Variants of hirudin which can be used as thrombin inhibitor have already been described. This is the case, for example, for the compounds described in Patents EP 209061 or EP 332523. Furthermore, synthetic analogues of hirudin fragments with anticoagulant properties have also been described; this is the case, for example, for the compounds claimed in Patents EP 276014, EP 291981, EP 291982 and EP 333356. Compared with the natural model, these shorter fragments (10 to 20 amino acids) offer the advantage of being "easier to handle": in particular their synthesis is simpler. More recently, the European Patent Application EP 0.372.503 claimed peptides which are analogues of hirudin in which a natural amino acid was replaced by a synthetic amino acid. Application EP 0.443.598 claims peptides which are analogues of hirudin in which a natural amino acid is replaced by a sulfonated or phosphonated derivative.

Applications PCT 91/01328, EP 443429 and EP 552999 claim analogues of hirudin in which the modifications affect both the introduction non-natural amino acids but also the introduction of sulfono-oxo or phosphono-oxo-amino-acids.

Finally, P. Bourdon et al. (FEBS Letters, 294(3), 163–166, 1991) have presented a structure-activity study relating to the interactions of peptides with thrombin.

DESCRIPTION OF THE INVENTION

The present invention relates more particularly to the compounds of formula (I):

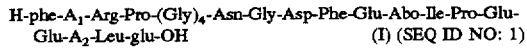

H-phe-A$_1$-Arg-Pro-(Gly)$_4$-Asn-Gly-Asp-Phe-Glu-Abo-Ile-Pro-Glu-Glu-A$_2$-Leu-glu-OH    (I) (SEQ ID NO: 1)

in which:

A$_1$ represents a proline residue (Pro), octahydroindole-2-carbonyl (Oic), 2-azabicyclo[2.2.1]heptane-3-carbonyl (Abh) or 2-azabicyclo[2.2.2]octane-3-carbonyl (Abo), A$_2$ represents a phenylalanine residue substituted in para or in meta by a group PO$_3$H$_2$ (Phe(pPO$_3$H$_2$), Phe (mPO$_3$H$_2$)), their addition salts with a pharmaceutically acceptable acid or base, each amino acid of the peptide sequence being optically pure and the carbon of each amino acid having the D or L configuration.

Among the pharmaceutically acceptable acids there may be mentioned, with no limitation being implied, hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic and camphoric acids and the like. Among the pharmaceutically acceptable bases there may be mentioned, with no limitation being implied, sodium hydroxide, potassium hydroxide, triethylamine, tertbutyl- amine and the like.

The invention also extends to the process for preparing derivatives of formula (I) which can be obtained by various methods such as sequential solid phase synthesis, synthesis of fragments and their coupling in solution, enzymatic synthesis, genetic synthesis by cloning and expression of genes in transformed bacteria or by various combinations of these techniques.

The general methods for solid phase peptide synthesis have been described by B. W. ERICKSON and R. B. MERRIFIELD ("The Proteins", Solid-phase Peptide Synthesis, 3rd edition, 257–527, 1976).

The solid phase synthesis can be carried out in an automatic machine which carries out in a repetitive and programmable manner deprotection, coupling and washing cycles necessary for the sequential introduction of the amino acids into the peptide chain. The amino acid, preferably the C-terminal amino acid, is attached to a resin conventionally used for the preparation of polypeptides, preferably a polystyrene cross-linked with the aid of 0.5 to 3.0% divinylbenzene and provided with activated residues such as chloromethylene or hydroxymethylene which permit the covalent attachment of the first amino acid onto the resin. The appropriate choice of resin permits the attachment of a carboxylic acid, amide or alcohol C-terminal functional group.

The amino acids are then introduced one by one in the order determined by the operator. Each synthetic cycle corresponding to the introduction of an amino acid, comprises a deprotection, preferably an N-terminal deprotection of the peptide chain, successive washes intended to remove the reagents or to swell the resin, a coupling with activation of the amino acid and new washes. Each of these operations is followed by a filtration carried out by virtue of the presence of a sintered glass incorporated into the reactor in which the synthesis is carried out.

The coupling reagents used are conventional reagents for peptide synthesis such as dicyclohexylcarbodiimide (DCC) and hydroxybenzotriazole (HOBT) or benzotriazol-1-yl-oxytris(dimethylamino)phosphonium hexafluorophosphate (BOP) or alternatively diphenylphosphorylazide (DPPA). Activations by formation of mixed anhydrides are also possible.

Each amino acid is introduced into the reactor in an approximately four-fold excess relative to the degree of substitution of the resin and in an approximately equivalent quantity relative to the coupling agents. The coupling reaction can be checked at each stage of the synthesis by the ninhydrin reaction test described by E. KAISER et al. (Analyt. Biochem., 34, 595, 1970).

After assembling the peptide chain on the resin, a treatment with a strong acid such as trifluoroacetic acid, or hydrofluoric acid in the presence of anisole, ethanedithiol or 2-methylindole serves to separate the peptide from the resin as well as to possibly liberate the peptide from its protecting groups. The compound is then purified by conventional purification techniques, especially, chromatography techniques.

The peptides of the present invention can also be obtained by coupling, in solution, of selectively protected peptide fragments which can be prepared either on a solid phase, or in solution. The use of protecting groups and the exploitation of their differential stability is analogous to the solid phase methods with the exception of the attachment of the peptide chain on to the resin. The C-terminal carboxylic group is protected, for example, by a methyl ester or an amide functional group. The activation methods during the couplings are also analogous to those used in the solid phase synthesis.

The compounds of formula (I) possess very advantageous pharmacological properties. They have anticoagulant and antithrombotic properties and can thus be used to prevent post-thromboembolic complications by dissolving the clots or as agents for preventing the extension of the thrombotic process by using them as direct and rapid action anticoagulants. The results obtained during pharmacological trials show that the compounds of the invention possess an antithrombotic activity which is greatly superior to that of a reference compound hirulog-1 (J. M. MARAGANORE et al., Biochem., 29, 7095–7101, 1990). This better activity is due to a greater inhibition of the catalytic site of thrombin. The subject of the present invention is also the pharmaceutical compositions containing, as active ingredient, at least one compound of general formula (I) or one of its addition salts with a pharmaceutically acceptable acid or base, alone or in combination with one or more non-toxic inert excipients or vehicles.

Among the pharmaceutical compositions according to the invention, there may be mentioned more particularly those which are suitable for oral, parenteral or nasal adminstration, plain or sugar-coated tablets, sublingual tablets, sachets, packets, gelatin capsules, glossettes, troches, suppositories, creams, ointments, skin gels, aerosols, ampoules to be taken orally, for injection and the like.

The dosage varies according to the age and the weight of the patient, the nature and the seriousness of the condition as well as the route of administration.

The latter may be oral, nasal, rectal or parenteral. Generally, it is between 0.05 and 30 mg for a treatment in a single or divided dose per 24 hours.

The following examples illustrate the invention and do not limit it in any manner.

In the examples below, the amino acids of which the abbreviations start by a capital letter are of L configuration. The amino acids of which the abbreviations start by a small letter are of D configuration.

The amino acid called Abo is of 3S configuration.

The amino acid called Oic is of 2S, 3aS, 7aS configuration.

Phe($pPO_3H_2$) represents the residue:

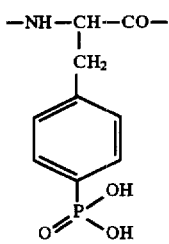

Phe($mPO_3H_2$) represents the residue:

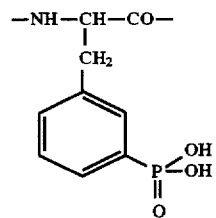

The compound described in preparation A is an intermediate which is useful in synthesis of the compounds of formula (I).

PREPARATION A: N-Fmoc-4-(dimethoxyphosphoryl)-L-phenylalanine (or Fmoc-Phe(pPO3(Me)2)

STAGE A: N-Boc-4[((trifluoromethyl)sulfonyl)oxy]-L-phenylalanine benzyl ester 7.4 mmol of triethylamine are added dropwise to a solution containing 6.8 mmol of N-Boc-L-tyrosine benzyl ester and 7.4 mmol of phenyl bis((trifluoromethyl)sulfonyl) amine in 10 ml of dichloromethane cooled on an ice bath. The mixture is stirred for 1 hour at 0° C. and 2 hours at room temperature. After adding 60 ml of diethyl ether, the organic phase is washed with water, with 1N sodium hydroxide, with water, then with a saturated sodium chloride solution, dried and evaporated. The expected product is then obtained in the form of an oil, after purification by chromatography on a silica column using as eluent a pentane/ethyl acetate mixture (80/20).

STAGE B: N-Boc-4-(dimethoxyphosphoryl)-L-phenylatanine benzyl ester

A suspension containing 1.1 mmol of the compound obtained in the preceding stage, 1.4 mmol of methylmorpholine, 1.32 mmol of (EtO)$_2$POH and 0.032 mmol of Pd(O)(pPH$_3$)$_4$ in 3 ml of anhydrous acetonitrile, is stirred at 70° C., under a nitrogen atmosphere, for 15 hours. After cooling, 40 ml of ethyl acetate are added. The organic phase is washed with 5% citric acid, with a 10% sodium hydrogen carbonate solution and then dried and evaporated. The expected product is then obtained, in the form of an oil, after purification by chromatography on a silica column using as eluent an ethyl acetate/pentane mixture (3/7).

STAGE C: N-Boc-4-(dimethoxyphosphoryl)-L-phenylalanine

A solution containing 14.4 mmol of the compound obtained in the preceding stage in 60 ml of methanol and 40 ml of water is reduced under a hydrogen pressure using 10% palladium/carbon as catalyst. After filtration and evaporation of the solvent, the expected product is obtained in the form of an oil.

STAGE D: Fmoc-Phe(pPO$_3$(Me)$_2$)

The compound obtained in the preceding stage is deprotected according to the technique described by B. Gutte et al., (J. Biol. Chem., 246, 1922–1941, 1971) and the Fmoc group is introduced according to the technique described by Carpino et al., (J. Org. Chem., 37, 3404–3409, 1972).

EXAMPLE 1

H-phe-Pro-Arg-Pro-(Gly)$_4$-Asn-Gly-Asp-Phe-Glu-Abo-Ile-Pro-(Glu)$_2$-Phe(pPO$_3$H$_2$)-Leu-glu-OH (SEQ ID NO: 2)

The compound of Example 1 is synthesized from 2 g of a resin substituted with 0.33 mmol/g of Fmoc-glu-(OtBu)-OH and following the following repetitive procedure:

| Operation No. | Function | Solvent/reagent | Repetition/time |
|---|---|---|---|
| 1 | washing | DMF | 2 × 2 min |
| 2 | deprotection | 20% piperidine/DMF | 1 × 5 min |
| 3 | deprotection | 20% piperidine/DMF | 1 × 15 min |
| 4 | washing | DMF | 3 × 2 min |
| 5 | washing | dichloromethane | 3 × 2 min |
| 6 | coupling | activated protected amino acid | 1 × 90 min |
| 7 | washing | DMF | 3 × 2 min |
| 8 | washing | isopropyl alcohol | 3 × 2 min |
| 9 | washing | dichloromethane | 3 × 2 min |

Each of these operations, carried out in 30 ml of solvent, with stirring and at room temperature, is followed by filtration through a sintered glass incorporated into the glass cell (reactor) in which the synthesis progresses. The filter retains the resin on which the growing peptide chain is attached.

The chosen protected amino acids were introduced in the following order: Fmoc-Leu-OH, Fmoc-Phe(pPO$_3$Me$_2$)-OH, Fmoc-Glu(OtBu)-OH, Fmoc-Glu(OtBu)-OH, Fmoc-Pro-OH, Fmoc-Ile-OH, Fmoc-Abo-OH, Fmoc-Glu(OtBu)-OH, Fmoc-Phe-OH, Fmoc-Asp(OtBu)-OH, Fmoc-Gly-OH, Fmoc-Asn-OH, Fmoc-Gly-OH, Fmoc-Gly-OH, Fmoc-Gly-OH, Fmoc-Gly-OH, Fmoc-Pro-OH, Fmoc-Arg(Pmc)-OH, Fmoc-Pro-OH, Fmoc-phe-OH.

The activation for the coupling (operation 6) is obtained at each cycle by dissolving 4 equivalents (2.64 mmol) of the amino acid protected with 360 mg of HOBt in 30 ml of DMF, then after 30 minutes at room temperature, by adding 618 mg of DCC. This solution is then immediately introduced into the reaction cell with 10 ml of dichloromethane.

The expected product is then obtained after conventional treatment of the resin with 95% trifluoroacetic acid (TFA) in the presence of anisole and ethanedithiol followed by a selective deprotection of the methyls of the phosphate group by a solution containing 90% TFA, 5% (CH$_3$)$_3$SiBr and 5% thioanisole. The peptide is then purified by preparative HPLC and freeze-dried.

Analysis of the product obtained is carried out after decomposition of the latter into amino acids by hydrolysis in 6N hydrochloric acid for 18 hours at 110 C and quantitative assay of the amino acids obtained by HPLC.

|  | Arg | Gly | Asp + Asn | Phe | Glu | Abo + Ile | Pro | Leu |
|---|---|---|---|---|---|---|---|---|
| Calculated | 1 | 5 | 2 | 2 | 4 | 2 | 3 | 1 |
| Found | 1.04 | 4.9 | 2.01 | 1.89 | 4.27 | 1.82 | 3.02 | 1.03 |

Mass spectrum (FAB): MH$^+$, m/$_z$=2381

The following examples were prepared using the process described in Example 1.

EXAMPLE 2

H-phe-Oic-Arg-Pro-(Gly)$_4$-Asn-Gly-Asp-Phe-Glu-Abo-Ile-Pro-(Glu)$_2$-Phe(pPO$_3$H$_2$)-Leu-glu-OH (SEQ ID NO: 3)

|  | Arg | Asp + Asn | Glu | Gly | Pro | Phe | Abo + Ile | Leu | Oic |
|---|---|---|---|---|---|---|---|---|---|
| Calculated | 1 | 2 | 4 | 5 | 2 | 2 | 2 | 1 | 1 |
| Found | 0.87 | 2.08 | 4.31 | 5.07 | 2.13 | 1.82 | 1.89 | 1.08 | 1.03 |

Mass spectrum (FAB): MH$^+$, m/$_z$=2435

EXAMPLE 3

(H-phe-Abh-Arg-Pro-(Gly)$_4$Asn-Gly-Asp-Phe-Glu-Abo-Ile-Pro-(Glu)$_2$-Phe(pPO$_3$H$_2$)-Leu-glu-OH (SEQ ID NO: 4))

EXAMPLE 4

H-phe-Abo-Arg-Pro-(Gly)$_4$-Asn-Gly-Asp-Phe-Glu-Abo-Ile-Pro-(Glu)$_2$-Phe(pPO$_3$H$_2$)-Leu-glu-OH (SEQ ID NO: 5)

EXAMPLE 5

H-phe-Pro-Arg-Pro-(Gly)$_4$-Asn-Gly-Asp-Phe-Glu-Abo-Ile-Pro-(Glu)$_2$-Phe(mPO$_3$H$_2$)-Leu-glu-OH (SEQ ID NO: 6)

PHARMACOLOGICAL STUDY OF THE COMPOUNDS OF THE INVENTION

EXAMPLE 6

Antithrombotic Activity

The experimental thrombosis model used is that of a venous thrombosis induced in male OFA rats by ligation of the vena cava inferior, (Millet et al., Thrombosis Res., 45: 123–133, 1987). The test animals are anesthetized by administration of sodium pentobarbital (50 mg/kg i.p.), 15 minutes before the ligation, the animals are treated with the test products via the i.v. route. The clot is withdrawn from the vena cava 25 minutes after the ligation, it is weighed after desiccation (24 hours at 60 C.). The compounds of the invention were tested at doses of 0.05, up to 1 mg/kg and compared with hirulog-1 (0.1 and 1 mg/kg). The results of this test show that the compounds of the invention permit a signification [sic] decrease in the weight of the clot which is greater than that observed with the reference compound hirulog-1: the compound of Example 1 is 20 times more active and the compound of Example 2 is 10 times more active than hirulog-1 on this model.

Decrease in the weight of the clot in %:

| Dose (mg/kg) | 0.05 | 0.1 | 0.5 | 1 |
|---|---|---|---|---|
| hirulog-1 |  | –0% |  | –46% |
| Example 1 | –45% | –64% | –71% | –83% |
| Example 2 |  | –45% | –62% |  |

EXAMPLE 7

Anticoagulant activity, measurement of the thrombin time and of the activated cephalin time In the presence of a standard quantity of thrombin or activated cephalin, a normal plasma coagulates within a defined and constant time called thrombin time (TT) and activated cephalin time (ACT) respectively. The extension of these coagulation times by pharmacological substances reflects an anticoagulant effect.

The in vitro effect of the products of the invention was measured on human plasma. Blood was collected by venous puncture in a tube containing citrate. After decantation (1200 g, 10 min), the plasma low in platelets is decanted so as to then carry out the coagulation tests. The compounds of the invention significantly extend the TT and ACT. The compound of Example 1 doubles the TT at the concentration of 0.05M and the ACT at the concentration of 0.14M. This activity is greater than that of hirulog-1, 0.07M and 0.2M respectively.

The effect of the products was tested ex vivo in OFA rats anesthetized with sodium pentobarbital (60 mg/kg i.p.) The carotid artery and the jugular vein are catheterized. After installation of the catheters, 1.5 cm$^3$ of arterial blood are collected over citrate (0.109M). 30 minutes later, the test product is administered in a volume of 1 ml by i.v. Arterial samples (1.5 cm$^3$) are then collected at 15 min, 3 min, 5 min, 15 min, 30 min and 60 min. At each collection of sample, 1.5 cm$^3$ of citrated physiological saline is reinjected into the animal via the carotid. The compounds of the invention significantly increase the TT and ACT ex vivo in rats. They increase the TT (multiplicative factor) and the ATC (multiplicative factor) more substantially than hirulog-1 and the duration of action is longer.

Increase in the TT:

|  | 1.5 min | 3 min | 5 min | 15 min | 30 min | 60 min |
|---|---|---|---|---|---|---|
| Example 1 (0.8 mg/kg) | >23 | >23 | >23 | 21 | 18 | 12 |
| hirulog-1 (0.8 mg/kg) | 13 | 11 | 9.8 | 6.6 | 4.2 | 2.2 |

Increase in the ACT:

|  | 1.5 min | 3 min | 5 min | 15 min | 30 min | 60 min |
|---|---|---|---|---|---|---|
| Example 1 (0.3 mg/kg) | 8.7 | 6.1 | 5.3 | 3.7 | 3.0 | 2.3 |
| hirulog-1 (0.8 mg/kg) | 3.8 | 3.2 | 2.6 | 2.1 | 1.6 | 1.3 |

EXAMPLE 8

Inhibition of thrombin and coagulation serine proteases

In order to evaluate in vitro the inhibitory activity of the products of the invention on human thrombin (Sigma, specific activity 3230 NIHU/mg), human fibrinogen (purified or plasmatic) (Fg) or the chromogenic substrate H-D-Phe-Pip-Arg-pNA (0.66 nM, S 2238, Kabi) were added to a given quantity of thrombin (0.7 or 2 nM) previously incubated with or without the test inhibitor (20 C, 10 min).

In order to evaluate in vitro the selectivity of these products towards various coagulation serine proteases, the same procedure was applied to purified human plasmin (2 nM, Stago), to purified human activated factor X (2 nM, Stago), to kallikrein (2 nM, sigma), to urokinase (2 nM, sigma), to plasminogen tissue activator (t-PA; 2 nM, Stago) and to purified human activated protein C (2 nM, Stago) using, as substrate, various paranitroanilide-containing peptides. The inhibitors, enzymes and substrates are diluted in the same buffer (0.01 mM phosphate buffer pH 7.4, containing 0.12M sodium chloride and 0.05% bovine serum albumin) and then distributed in a polystyrene microplate in a volume of 50 l.

The fibrin formed by thrombin or the paranitroanilide liberated by the action of the serin protease is measured spectrophotometrically at 405 nm after reacting for 15 to 30 minutes at 20° C. The results presented below show the inhibition of thrombin by the substances of the invention compared with hirulog-1 with respect to fibrinogen and the chromogenic substrate. The results are expressed in IC$_{50}$ value: the concentration in nM which inhibits the enzymatic activity by 50%. The compounds of the invention have a higher activity than that of hirulog-1. This is particularly the case in the presence of the chromogenic substrate, demonstrating a superior inhibitory activity of the products of the invention on the catalytic site of thrombin.

|  | IC$_{50}$ Fibrinogen | IC$_{50}$ Chromogenic substrate |
|---|---|---|
| Example 1 | 6.1 | 18 |
| Example 2 | 4.0 | 15 |
| hirulog-1 | 10.2 | 215 |

Like hirulog-1, the products of the invention are extremely selective for thrombin since the IC$_{50}$ values with respect to the other fibrinolysis and coagulation serine proteases are all greater than 33M.

EXAMPLE 9

Pharmaceutical composition: solution for injection

| Solution for injection: | |
|---|---|
| Compound of Example 1: 5 mg | |
| Distilled water for injection, qs: 25 ml | |
| Tablet: | |
| Preparation formula for 1000 tablets | |
| Compound of Example 1 | 5 g |
| Wheat starch | 10 g |
| Maize starch | 10 g |
| Lactose | 60 g |
| Magnesium stearate | 2 g |
| Silica, hydroxypropyl cellulose | 2 g |

An additional envelope will ensure the gastroresistance of the galenic form.

We claim:

1. A compound of the formula (I)

H-D-Phe-$A_1$-Arg-Pro-(Gly)$_4$-Asn-Gly-Asp-Phe-Glu-Abo-Ile-Pro-Glu-Glu-$A_2$-Leu-D-Glu-OH (SEQ ID NO: 1)  (I)

in which:

$A_1$ represents octahydroindole-2-carbonyl (Oic), 2-azabicyclo[2.2.1]heptane-3-carbonyl (Abh), or 2-azabicyclo[2.2.2]octane-3-carbonyl (Abo), $A_2$ represents a phenylalanine residue substituted in para or in meta position by a group $PO_3H_2$ (Phe(pPO$_3$H$_2$), Phe(mPO$_3$H$_2$)), or an addition salt thereof with a pharmaceutically-acceptable acid or base, each amino acid of the peptide sequence being optically pure and the alpha carbon of each amino acid having the D or L configuration.

2. The compound of formula (I) as claimed in claim 1, such that $A_2$ represents a (pPO$_3$H$_2$)phenylalanine residue.

3. The compound of formula (I) as claimed in claim 1, which is H-D-phe-Oic-Arg-Pro-(Gly)$_4$-Asn-Gly-Asp-Phe-Glu-Abo-Ile-Pro-(Glu)$_2$-Phe(pPO$_3$H$_2$)-Leu-D-Glu-OH (SEQ ID NO: 3).

4. A method for treating an animal or human afflicted with a condition requiring an anticoagulant comprising the step of administering to the living body an amount of a compound of claim 1 which is effective for alleviation of said condition.

5. A pharmaceutical composition useful as an anticoagulant comprising as active principle an effective anticoagulant amount of a compound as claimed in claim 1, together with one or more pharmaceutically-acceptable excipients or vehicles.

6. The compound of formula (I) as claimed in claim 1, which is H-D-Phe-Abh-Arg-Pro-(Gly)$_4$-Asn-Gly-Asp-Phe-Glu-Abo-Ile-Pro-(Glu)$_2$-Phe(pPO$_3$H$_2$)-Leu-D-Glu-OH (SEQ ID NO: 4).

* * * * *

UNITED STATES PATENT AND TRADEMARK OFFICE
CERTIFICATE OF CORRECTION

PATENT NO.    : 5,786,330
DATED         : July 28, 1998
INVENTOR(S)   : Jean-Luc Fauchere, Christophe Thurieau,
                Tony Verbeuren, Alain Rupin, Serge Simonet It is certified that error appears in the above-indentified patent and that said Letters Patent is hereby corrected as shown below:

Col. 4, line 34; "phenylatanine" should read
-- phenylalanine --.

Col. 7, third line of the second table; "(0.3 mg/kg)"
should read -- (0.8 mg/kg) --.

Col. 11, (2) INFORMATION FOR SEQ ID NO:4:, sixth paragraph
under (ix) FEATURE:, line 2 under (D) OTHER INFORMATION:;
"/ note="Phe(pPOcH2)"" should read
-- / note="Phe(pPO3H2) --.

Signed and Sealed this

Twelfth Day of January, 1999

Attest:

Attesting Officer

Acting Commissioner of Patents and Trademarks